United States Patent
Brehm

(10) Patent No.: US 9,901,427 B2
(45) Date of Patent: Feb. 27, 2018

(54) SEMI-FINISHED PRODUCT FOR MANUFACTURING DENTAL PROSTHESES, ABUTMENT AND METHOD FOR PRODUCING DENTAL PROSTHESES

(71) Applicant: bredent GmbH & Co. KG, Senden (DE)

(72) Inventor: Peter Brehm, Senden (DE)

(73) Assignee: bredent GmbH & Co. KG, Senden (DE)

( * ) Notice: Subject to any disclaimer, the term of this patent is extended or adjusted under 35 U.S.C. 154(b) by 0 days.

(21) Appl. No.: 14/902,356

(22) PCT Filed: Jul. 4, 2014

(86) PCT No.: PCT/EP2014/064331
§ 371 (c)(1),
(2) Date: Dec. 31, 2015

(87) PCT Pub. No.: WO2015/001088
PCT Pub. Date: Jan. 8, 2015

(65) Prior Publication Data
US 2016/0199159 A1    Jul. 14, 2016

(30) Foreign Application Priority Data

Jul. 4, 2013   (DE) .................. 10 2013 107 067

(51) Int. Cl.
*A61C 8/00*     (2006.01)
*A61C 13/00*    (2006.01)
(Continued)

(52) U.S. Cl.
CPC .......... *A61C 13/0022* (2013.01); *A61C 8/005* (2013.01); *A61C 13/0006* (2013.01);
(Continued)

(58) Field of Classification Search
CPC . A61C 13/0022; A61C 13/006; A61C 13/082; A61C 13/083; A61C 13/09;
(Continued)

(56) References Cited

U.S. PATENT DOCUMENTS 5,198,174 A * 3/1993 Nakagawa .......... B29C 33/0033
                                                      264/512
5,240,537 A * 8/1993 Bodicky ............. A61M 25/001
                                                      156/244.13
(Continued)

FOREIGN PATENT DOCUMENTS

WO    2008/069620 A1    6/2008

OTHER PUBLICATIONS

International Search Report of PCT/EP2014/064331, dated Oct. 13, 2014.

*Primary Examiner* — Joseph S Del Sole
*Assistant Examiner* — Emmanuel S Luk
(74) *Attorney, Agent, or Firm* — Collard & Roe, P.C.

(57) ABSTRACT

A semi-finished product produces dental prostheses, in particular abutments, and a method produces a semi-finished product for manufacturing dental prostheses. The semi-finished product includes a base body (GK) which has a channel (KA) passing through the base body (GK), a hollow-cylindrical anchoring element being embodied on the inner surface thereof (IF). The base body (GK) covers the anchoring element (VA) at least partially over the whole area with a thermoplastic synthetic material.

12 Claims, 8 Drawing Sheets

Figure 1:
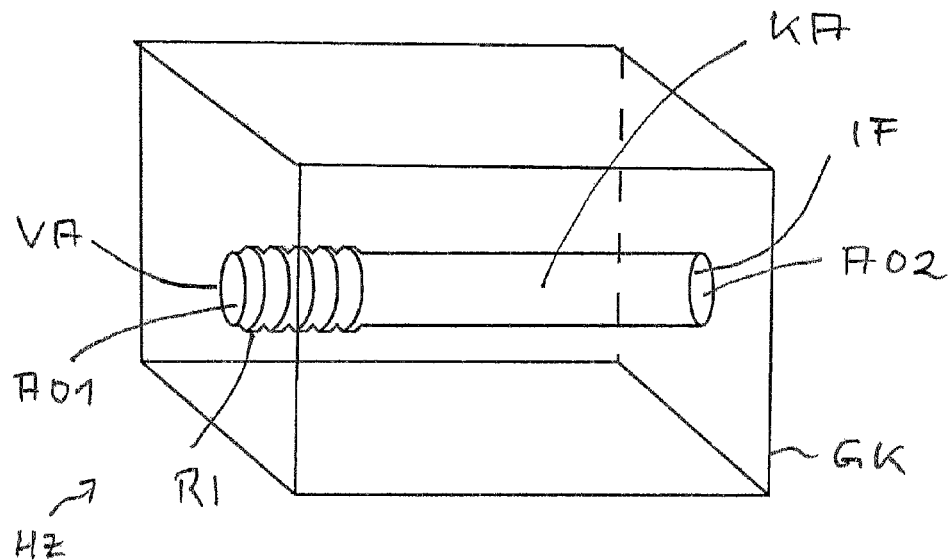

(51) Int. Cl.
*A61C 13/08* (2006.01)
*A61C 13/083* (2006.01)
*A61C 13/09* (2006.01)
*B29C 43/00* (2006.01)
*B29C 43/18* (2006.01)
*B29C 43/52* (2006.01)
*B29K 101/12* (2006.01)
*B29K 105/06* (2006.01)
*B29K 105/00* (2006.01)
*B29L 31/00* (2006.01)

(52) U.S. Cl.
CPC .......... *A61C 13/082* (2013.01); *A61C 13/083* (2013.01); *A61C 13/09* (2013.01); *B29C 43/003* (2013.01); *B29C 43/18* (2013.01); *B29C 43/52* (2013.01); *B29K 2101/12* (2013.01); *B29K 2105/06* (2013.01); *B29K 2105/251* (2013.01); *B29L 2031/7532* (2013.01)

(58) Field of Classification Search
CPC ... A61C 8/005; A61C 13/0006; B29C 43/003; B29C 43/18; B29C 43/52; B29K 2101/12; B29K 2105/06; B29L 2031/7532
See application file for complete search history.

(56) References Cited

U.S. PATENT DOCUMENTS

| | | | | |
|---|---|---|---|---|
| 5,256,237 A * | 10/1993 | Maas | ...................... | B29C 43/18 156/156 |
| 5,695,337 A * | 12/1997 | Tyszblat Sadoun | . | A61C 8/0048 433/173 |
| 6,358,052 B1 * | 3/2002 | Lustig | ................. | A61C 8/0001 433/174 |
| 6,482,284 B1 * | 11/2002 | Reidt | ................... | A61C 13/0022 156/200 |
| 6,537,069 B1 * | 3/2003 | Simmons, Jr. | ......... | A61C 8/001 433/173 |
| 6,669,875 B2 * | 12/2003 | Meyertholen | ...... | A61C 13/0003 264/138 |
| 7,563,397 B2 * | 7/2009 | Schulman | .......... | A61C 13/0003 164/34 |
| 8,844,139 B2 * | 9/2014 | Johnson | ............ | A61C 13/0004 29/896.1 |
| 8,906,981 B2 * | 12/2014 | Yang | .................... | A61K 6/0002 523/115 |
| 8,973,269 B2 * | 3/2015 | Johnson | ............. | A61C 13/0004 264/16 |
| 9,345,561 B2 * | 5/2016 | Johnson | ............ | A61C 13/0022 |
| 2001/0055743 A1 * | 12/2001 | Yeung | .................... | A61C 8/005 433/173 |
| 2005/0136378 A1 * | 6/2005 | Ennajimi | ............... | A61C 8/005 433/173 |
| 2006/0163774 A1 * | 7/2006 | Abels | ...................... | B28B 11/12 264/293 |
| 2008/0254414 A1 * | 10/2008 | McGuire | ........... | A61C 13/0022 433/223 |
| 2010/0323324 A1 * | 12/2010 | Kim | ...................... | A61C 8/005 433/173 |
| 2011/0065065 A1 * | 3/2011 | Mormann | ........... | A61C 8/0051 433/201.1 |
| 2011/0207086 A1 * | 8/2011 | Yang | .................... | A61K 6/0017 433/215 |
| 2012/0251979 A1 * | 10/2012 | Karim | .................... | A61C 8/005 433/201.1 |
| 2014/0234802 A1 * | 8/2014 | McDermott | ......... | A61C 13/081 433/202.1 |
| 2015/0216635 A1 * | 8/2015 | Schweiger | ........... | A61K 6/0005 433/173 |

* cited by examiner

SEMI-FINISHED PRODUCT FOR MANUFACTURING DENTAL PROSTHESES, ABUTMENT AND METHOD FOR PRODUCING DENTAL PROSTHESES

CROSS REFERENCE TO RELATED APPLICATIONS

This application is the National Stage of PCT/EP2014/064331 filed on Jul. 4, 2014, which claims priority under 35 U.S.C. § 119 of German Application No. 10 2013 107 067.1 filed on Jul. 4, 2013, the disclosure of which is incorporated by reference. The international application under PCT article 21(2) was not published in English.

The invention relates to a semifinished product for the fabrication of dental prosthetic arrangements as well as to an abutment. Beyond this, the invention relates to a method for the production of dental prosthetic arrangements.

Abutments are known from the general prior art and are used in various ways in the field of dental prostheses. In general, what is understood by an abutment is a mounting element used for fastening of crowns or dental bridges in dentistry. Beyond this, abutments are also known as primary or secondary holders of strut-like or telescoping dental prosthetic arrangements.

In order to create the desired fastening capability, abutments are usually prepared by means of a metallic pin, which in combination with an implant anchored in a jawbone functions as an anchoring point. A crown, for example, is disposed on the opposite side. Usually abutments are made of titanium. As an example, a crown may then be adhesively bonded to or screwed onto the abutment.

Implants are likewise known from the general prior art. For anchoring in a jawbone, implants have a screw joint, wherein a tooth crown or the abutment, for example, may then be disposed on the opposite side.

Besides the production of implants or abutments and crowns in dental laboratories specially equipped for the purpose, systems in which the dental prosthetic elements can be made during treatment of the patient by the dentist have also proved themselves in recent years. Besides the cost savings attainable therewith, a treatment more comfortable for the patient is also achieved, since an individual adaptation to the circumstances of the patient can be made possible without the need for further iterations to be performed by a dental technician. The individual machinability by a dentist thus permits a very efficient fabrication of dental prosthetic arrangements. To use the English terminology, these systems are also known as chairside systems. This term makes it clear that the fabrication of dental prosthetic arrangements takes place directly at or next to the dental chair.

Known examples for chairside systems are provided with a visual recording system, which permits, for the individual case, the generation of dental prosthetic arrangements which, after processing in a computer, are implemented in an appropriate milling program. The milling program delivers corresponding instructions for machining a semifinished product in such a way that it represents the desired dental prosthetic arrangement. Known semifinished products of this type usually have an injected-molded titanium reinforcement, in which a titanium base, for example, is able to engage. The semifinished product usually consists of a sintered ceramic material.

It is known that high forces, which may lead to mechanical loads, often occur during use of dental prosthetic arrangements, and so it is possible that mechanical damage may occur.

Consequently, a need exists in the art to overcome the above-mentioned disadvantages and to further improve known semifinished products or, in general, also dental prosthetic arrangements.

It is therefore the task of the invention to create a semifinished product or an abutment in which a further improvement with respect to the mechanical properties is achieved. Furthermore, it is intended that a method for the production of a dental prosthetic arrangement be specified that permits a simple production with improved mechanical properties.

This task is accomplished by the features of the independent claims. Further advantageous configurations of the invention are respectively subject matter of the dependent claims. These may be combined with one another in technologically logical manner. The description, especially in conjunction with the drawing, additionally characterizes and specifies the invention.

According to the invention, a semifinished product for the fabrication of dental prosthetic arrangements, especially of abutments, is created, which comprises the following: a one-colored or multi-colored base block, which has, passing through the base block, a channel, on the inside face of which a hollow-cylindrical anchoring element is formed, wherein the base block covers the anchoring element with a thermoplastic synthetic material in one-colored or multi-colored form at least partly over the full surface.

Accordingly, an anchoring element that is disposed within the base block by means of hot-pressing, for example, of a thermoplastic synthetic material, is incorporated into a semifinished product. Whereas the base block of the thermoplastic synthetic material can be further processed to the desired dental prosthetic arrangement in further machining steps with an appropriate milling or grinding algorithm, the anchoring element establishes a capability of appropriately holding the dental prosthetic arrangement created in this way. For this purpose the anchoring element is formed in the shape of a hollow cylinder, so that either a screw channel or an adhesive bonding face is created that can be used for the anchoring. By virtue of the interstice-free joint between the anchoring element and the base block, the dental prosthetic arrangement is capable of absorbing high forces without then loosening or splintering. This has the consequence that high chewing forces can be absorbed, and so the dental prosthetic arrangement created with this semifinished product withstands high mechanical loads. It is also possible to create two-colored and if necessary multi-colored semifinished products, so that, for example, a portion disposed later in the gums during use of the semifinished product as a dental prosthetic arrangement is finished with a pink partial coloration, in order to achieve an adaptation to the visual impression of real teeth, especially in a front-teeth region.

The anchoring element may be furnished with a coating, wherein the coating, preferably of the thermoplastic material, is applied on a side facing away from the inside surface.

According to this embodiment, an adhesive joint face, which may likewise consist of the thermoplastic material, is created, especially for adhesive bonding of the dental prosthetic arrangement. Consequently, it is possible to improve the durability of the adhesive joint site further.

The anchoring element may have a roughened surface on a side facing the inside surface.

Experiments have shown that a roughened surface may promote the joining of the anchoring element with the base block by means of hot pressing. For this purpose the roughened surface may have a grain texture in the range of several 100 μm, wherein the exact configuration is dependent on the materials used.

According to a further embodiment, the anchoring element is made of a non-noble metal, preferably titanium or a titanium alloy, of a ceramic, especially aluminum oxide or zirconium dioxide, or of a fiber-reinforced material suitable for dental purposes.

Titanium is best suited in the human body for use in dental prosthetics. Stress-free structures are obtained especially in conjunction with a thermoplastic synthetic material, wherein the base block consisting of the thermoplastic synthetic material is joined in gap-free relationship to the anchoring element. In this connection it is surprisingly found that the hot-pressed synthetic material forms, with the non-noble metal, a particularly stable joint, which beyond this is free of cracks or gaps. One supposition consists in the fact that the metal oxide formed on the surface of the non-noble metal bonds, for example, with polymer chains of the base block, which imparts particularly high-performance properties to the semifinished product. Ceramic material such as aluminum oxide or even zirconium dioxide may likewise be used. Beyond this, it has been shown that the use of fiber-reinforced material imparts adequate stability to the anchoring element, and so this also may be adopted for use in a semifinished product.

In a further embodiment, the anchoring element is furnished with a base element protruding out of the base block.

In addition to the embodiment depicted up to now, in which the anchoring unit may be used, for example, as injection-molded titanium reinforcement for the seating of an adhesive base for different implant systems, the base element according to this embodiment is brought together with the anchoring element in the base block. Thus the base element and the anchoring element may be constructed in one piece, and so they are injection-molded together in the thermoplastic synthetic material of the base block. It is likewise possible, however, to join the base element, for example by means of a mechanical joint, with the anchoring element.

The base element may be provided with a holding pin, introducible into an implant, which preferably has a non-rotationally-symmetric cross section or comprises an implant anchorable in a jawbone.

Accordingly, it is possible to use the semifinished product together with the base element as a mounting block for a dental prosthetic arrangement. The base element then functions for anchoring in a jawbone, which is achieved either via the holding pin introducible into the implant or itself has already been formed as the implant, so that it can be incorporated into the jawbone. Accordingly, a dental prosthetic arrangement is created that may be inserted into the jaw of a patient without further machining steps.

According to a further embodiment, the base element is fastened in the anchoring element by means of adhesive bonding.

According to this embodiment, the base element functions as the adhesive base, which is adhesively joined to the anchoring element.

The base element may be furnished with a surface structure that is introducible into a corresponding surface structure of the anchoring element.

This supports the adhesive fastening of the anchoring element with the base element, so that a durable and reliable adhesive joint can be created.

In addition to the adhesive joint, the base element may now also be fastened in the anchoring element with a retention mechanism, which preferably is constructed as a quarter-turn lock. This feature may also be implemented instead of the adhesive joint and it provides for a reliable joint between base element and anchoring element.

The base element may be made of a non-noble metal, preferably titanium or a titanium alloy, of a ceramic, especially aluminum oxide or zirconium dioxide or of a material suitable for dental purposes.

Titanium or titanium alloys in particular are preferably used in the above-described adhesive bonding between base element and anchoring element. However, the other materials mentioned are not excluded.

In a further embodiment, the base block can be joined to a holding element, which is used as a holder in a machining device.

Accordingly, it is possible with the semifinished product according to the invention to construct so-called chairside systems, in which the base block is formed into the desired shape by means of a computer-assisted, mechanical machining step, for example milling or grinding.

This holding element may be constructed in such a way that it can be introduced into the anchoring element or into the base element.

Accordingly, a stable and reliable holding of the base block of the semifinished product is created by means of the holding element. For this purpose the holding element and the channel may be disposed to engage axially one inside the other, so that the holding element and the channel are aligned with one another. As the consequence of this, the longitudinal axis of the channel coincides with a longitudinal axis of the holding element, so that the semifinished product with the anchoring element can be incorporated into the so-called A-axis of the machining device.

However, the holding element and the channel may also have a different direction along their longitudinal axes, preferably a right angle.

Accordingly, the holding element is formed with a different axial relationship in comparison with the channel, wherein usually the so-called Y-axis finds use in chairside systems. This embodiment is advantageously used when the anchoring element or the base element are not supposed to coincide with the axis of the machine holder.

The holding element may be injection-molded into the base block. However, it is also provided that the holding element is formed in one piece together with the one-colored or multi-colored base block.

Accordingly, a one-piece semifinished product is created that can be further processed in common machining devices. This is achieved either by injection molding or one-piece forming.

In another embodiment it is provided that the holding element is adhesively bonded with the base block, so that an, adhesive joint is obtained between the base block and the holding element.

In this case it may be advantageous when the holding element is furnished at least on the side facing the adhesive joint with a coating, preferably of the thermoplastic synthetic material.

Accordingly the adhesive bond between the holding element and the base block is assisted by the fact that the holding element is coated in the region of the adhesive joint with the same thermoplastic synthetic material.

PEEK, PAEK or PEKK come into consideration as thermoplastic synthetic materials. As biocompatible materials, PEEK (abbreviation for polyether ether ketone), PAEK (abbreviation for polyaryl ether ketone) or PEKK (abbreviation for polyether ketone ketone) are substantially physiologically inert for use in medicine and consequently are irritation-free for the patient. Beyond this, however, the said thermoplastic synthetic materials also exhibit high loadability, and so high fracture strengths can also be achieved. Consequently this material offers high safety margins, which is important in particular for use of implants or abutments in the side-teeth region.

The use of the above-described semifinished product according to the invention in a machining device for the fabrication of abutments, implants or crowns is particularly advantageous when the machining device is preferably able to execute computer-assisted machining of the base block.

According to the invention, an abutment is also specified that comprises a one-colored or multi-colored base block, which has, passing through the base block, a channel, on the inside face of which a hollow cylindrical anchoring element is formed, wherein the base block covers the anchoring element with a thermoplastic synthetic material of PEEK, PEKK or PAEK in one-colored or multi-colored form at least partly over the full surface.

Accordingly an anchoring element, which is surrounded by a thermoplastic synthetic material, by means of hot-pressing, for example, is incorporated into an abutment. Whereas the base block can be produced with the desired abutment shape from the thermoplastic synthetic material, the anchoring element constitutes a capability of inserting the dental prosthetic arrangement created in this way into an implant, for example, or of furnishing it with a mounting element.

Finally, a method is specified for the production of dental prosthetic arrangements, especially of abutments or semifinished products for the fabrication of abutments, implants or crowns, that includes the steps listed in the following. First a preparation of a hollow cylindrical anchoring element is carried out. Thereupon the hollow cylindrical anchoring element is surrounded with a synthetic material granulate or synthetic material pellets of a thermoplastic synthetic material. Then a hot-pressing of the synthetic material granulate or of the synthetic material pellets is carried out, so that a base block is formed that has, passing through the base block, a channel, on the inside face of which the hollow cylindrical anchoring element is disposed, wherein the base block covers the anchoring element with the thermoplastic synthetic material at least partly over the full surface.

By means of hot pressing, an anchoring element is surrounded by a thermoplastic synthetic material, so that it is disposed inside a base block. Whereas the base block of the thermoplastic synthetic material can be further processed to the desired dental prosthetic arrangement in further machining steps with an appropriate milling or grinding algorithm, the anchoring element establishes a capability of appropriately holding the dental prosthetic arrangement created in this way. Once again, PEEK, PEKK, PAEK come into question as thermoplastic synthetic materials.

Beyond this, in a further embodiment of the method, a holding element used as a holder in a machining device is formed during hot-pressing, wherein the machining device performs preferably computer-assisted machining of the base block (GK).

Furthermore, the implant joint geometry on the semifinished product can be formed during hot-pressing.

Accordingly, the holding element can be created together with the base block in a single production step, which permits a particularly cost-favorable fabrication of a dental prosthetic arrangement or respectively of a semifinished product.

In a further embodiment of the method, a portion of the dental prosthetic arrangement disposed in the gums is finished with a pink partial coloration.

Accordingly it is possible to create a two-colored or if necessary even multi-colored dental prosthetic arrangement, in which an adaptation to the visual impression of real teeth is achieved, especially in a front-teeth region, so that the wearing of a dental prosthetic arrangement is not very obvious to an observer. Thereby the acceptance of dental prosthetic arrangements is enhanced.

Figure 2:
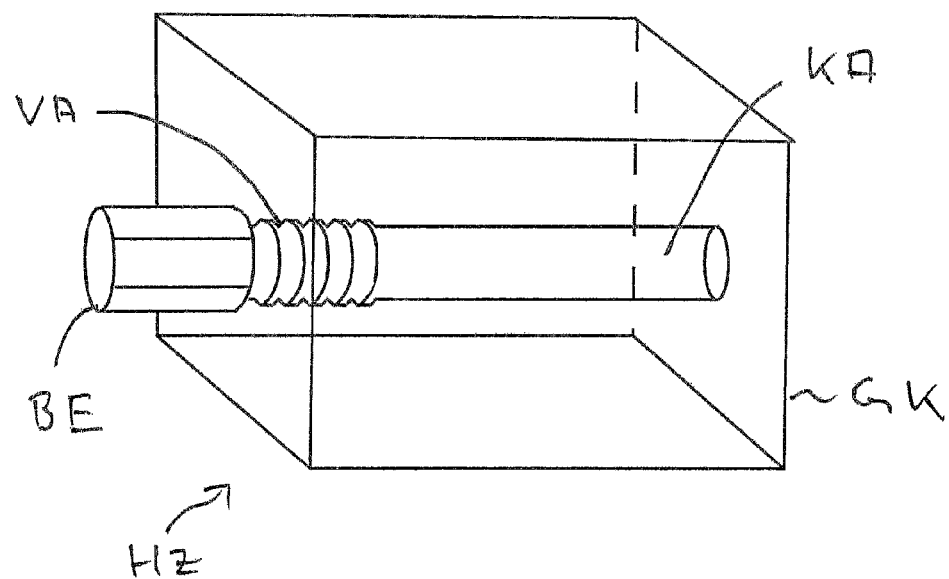
Figure 3:
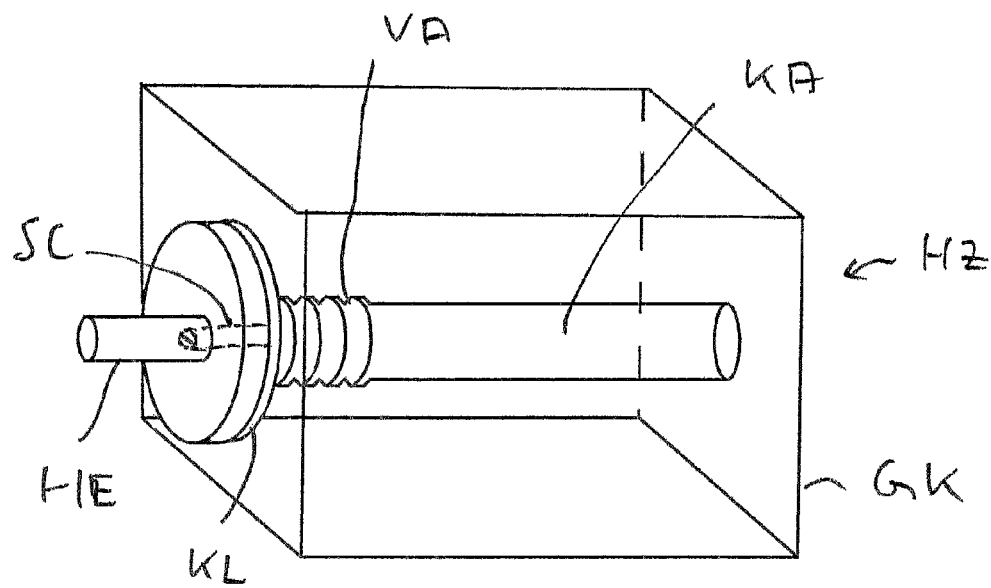
Figure 4:
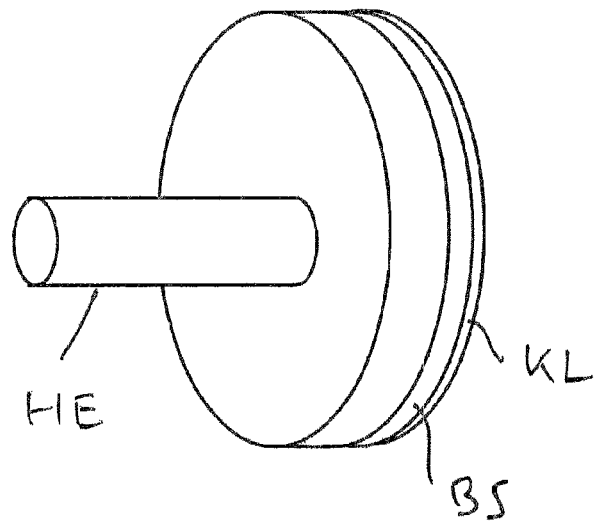
Figure 5:
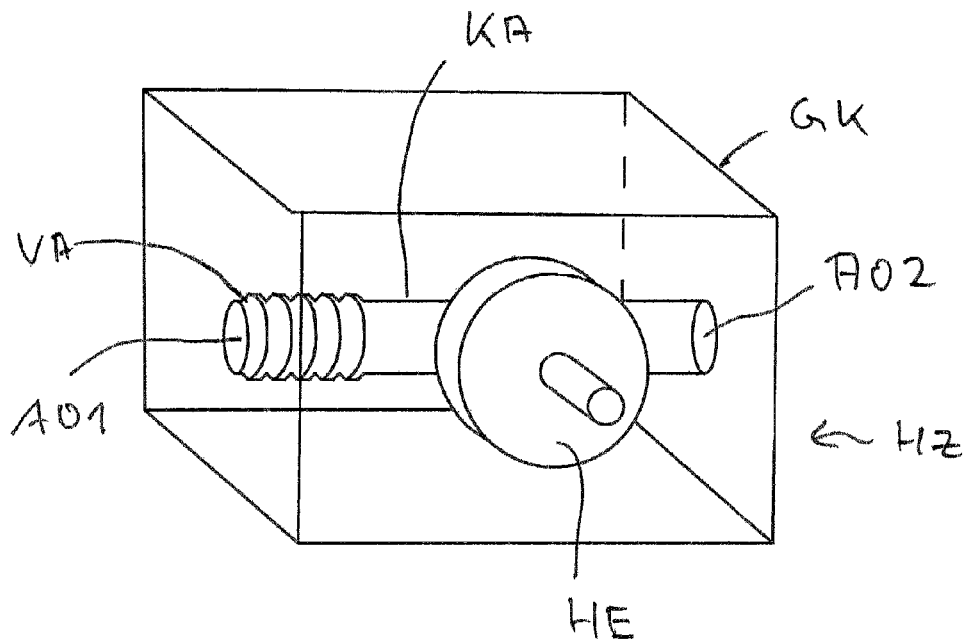
Figure 6:
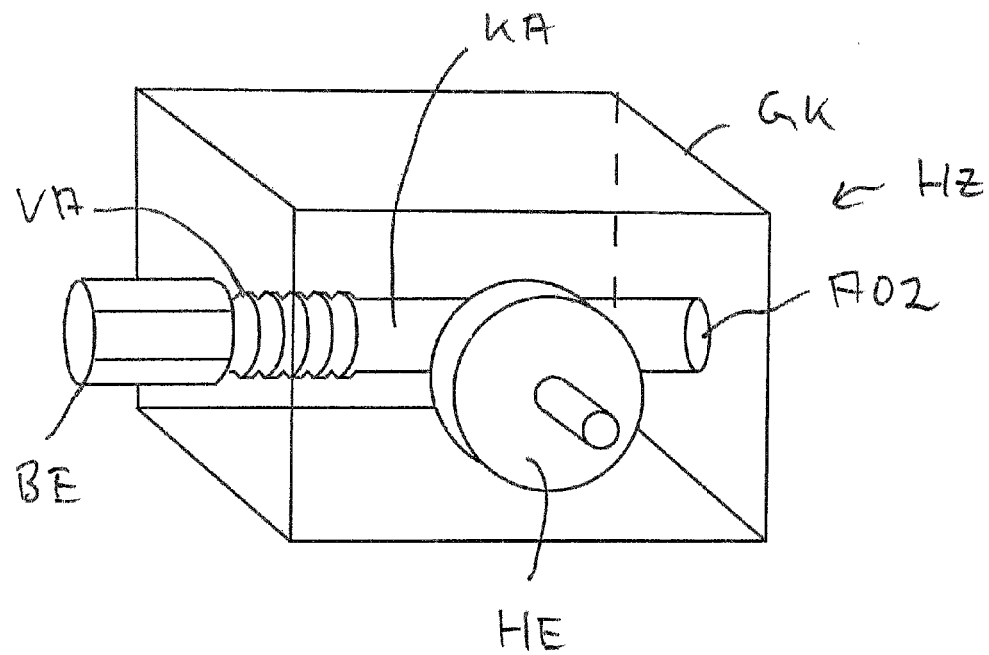
Figure 7:
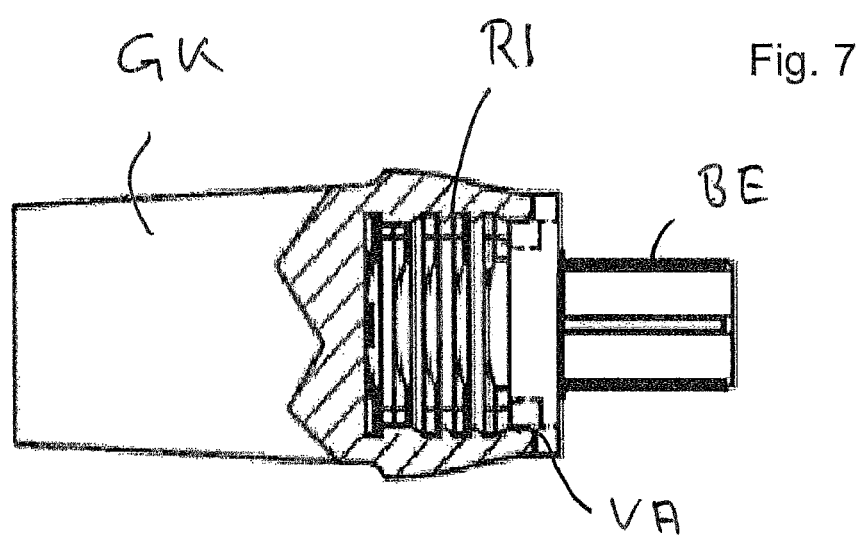
Figure 8:
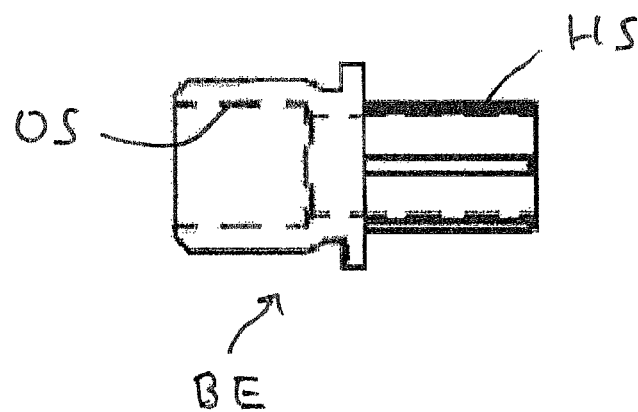
Figure 9:
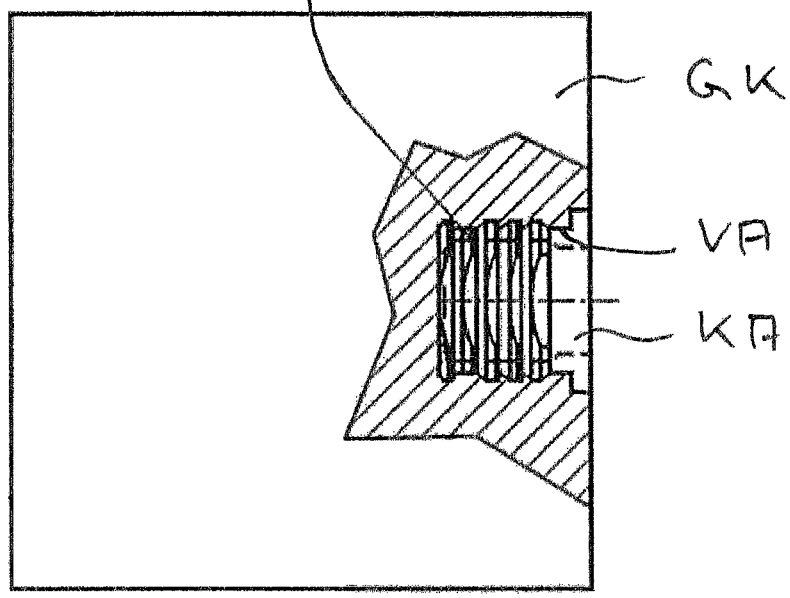
Figure 10:
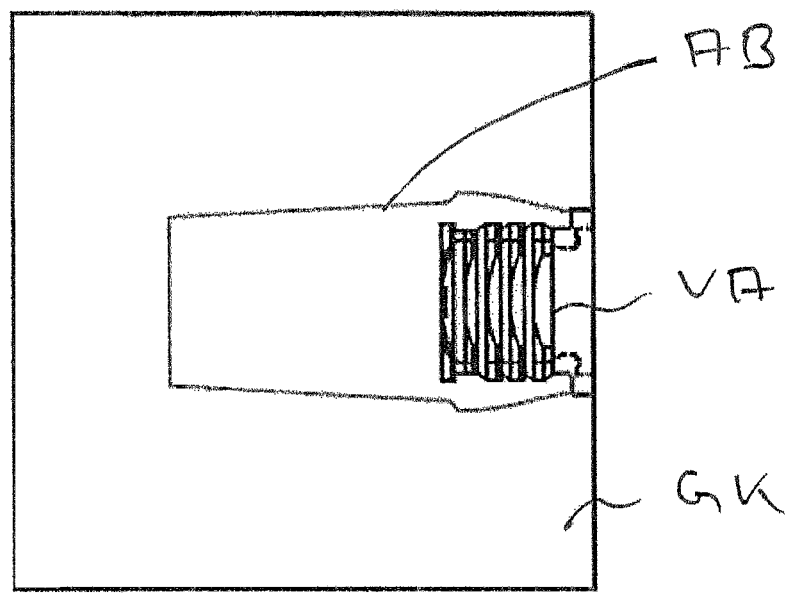
Figure 11A:
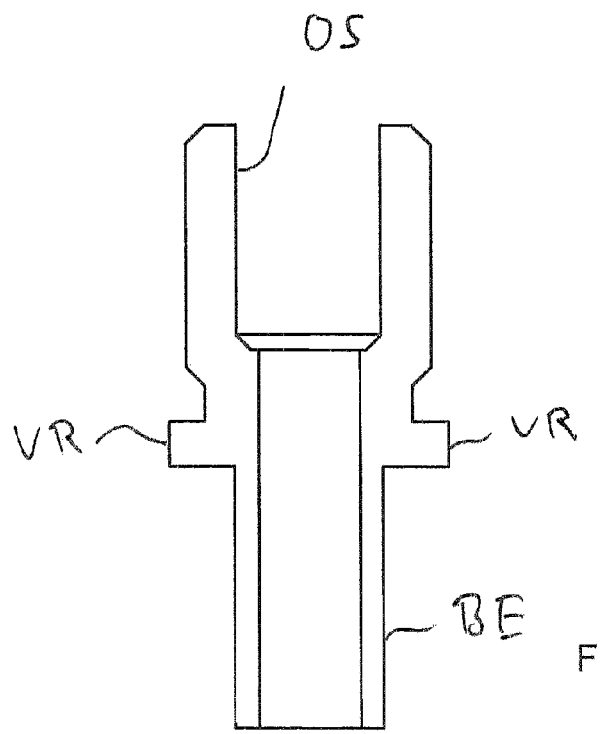
Figures 11B, 11C:
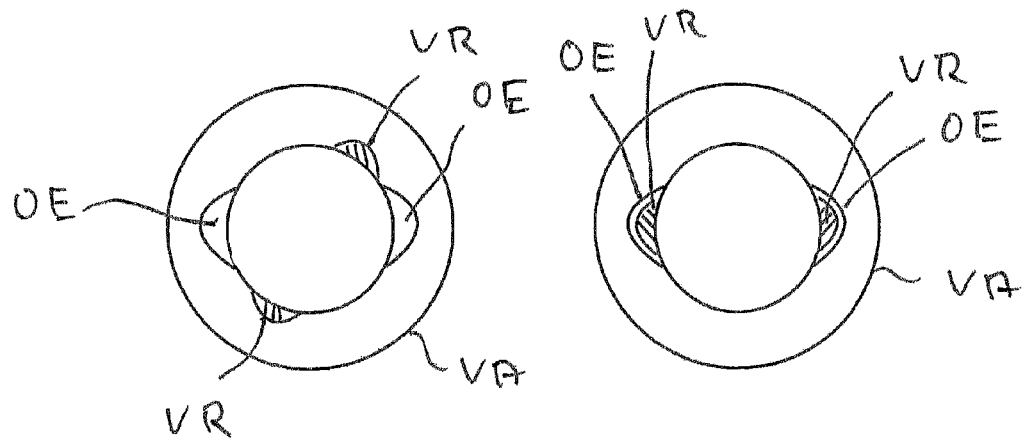
Figure 12:
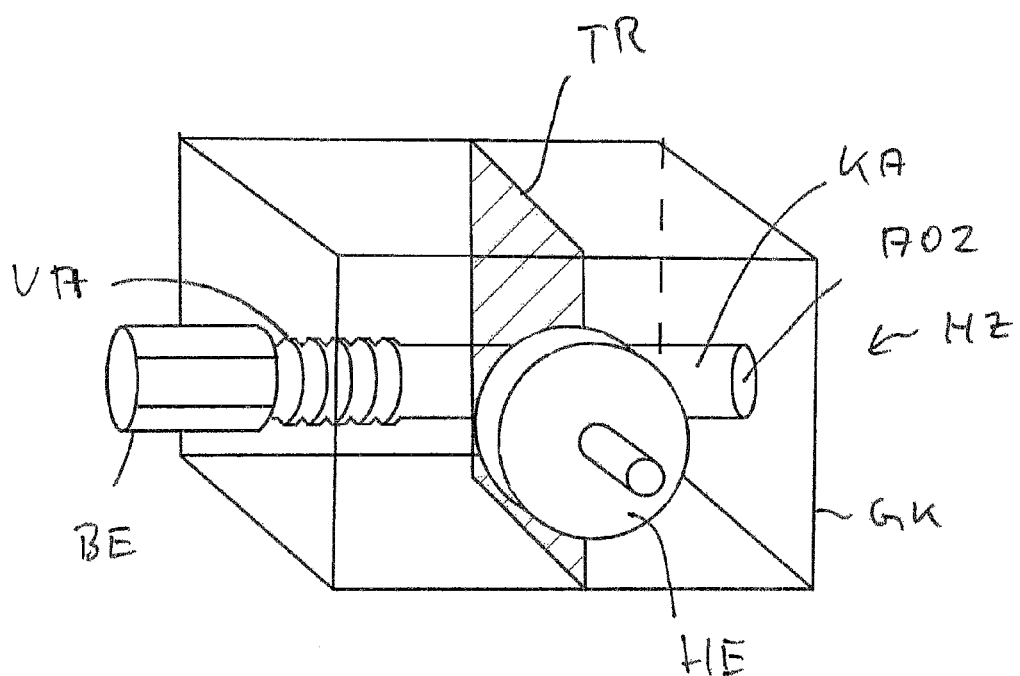
Figure 13:
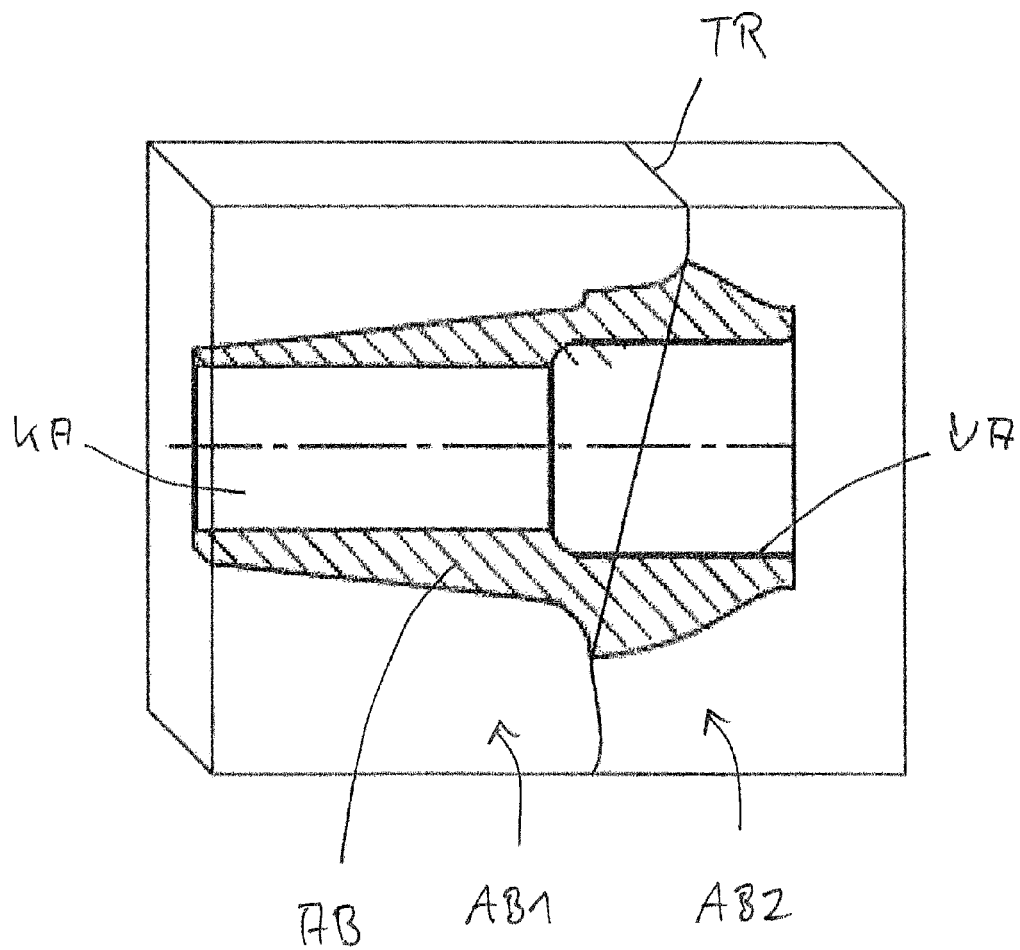

Some exemplary embodiments will be explained in more detail hereinafter on the basis of the drawings, wherein:

FIG. 1 shows a semifinished product according to the invention in a perspective side view according to a first embodiment, FIG. 2 shows a semifinished product according to the invention in a perspective side view according to a second embodiment, FIG. 3 shows a semifinished product according to the invention in a perspective side view according to a third embodiment, FIG. 4 shows the holding element of the embodiment according to FIG. 3 in an enlarged representation, FIG. 5 shows a semifinished product according to the invention in a perspective side view in a further embodiment, FIG. 6 shows a semifinished product according to the invention in a perspective side view according to a further embodiment, FIG. 7 shows an enlarged representation of a detail of the semifinished product according to the invention in a top view, FIG. 8 shows a base element for use in the semifinished product according to the invention in a top view, FIG. 9 shows a sectional view of a semifinished product according to the invention, FIG. 10 shows a detail view of the semifinished product according to the invention during further processing, FIG. 11 (A) to (C) show a base element with retentive regions in a cross sectional view or in a top view respectively, FIG. 12 shows a further sectional view of a semifinished product according to the invention, and FIG. 13 shows a sectional view of an abutment according to the invention.

In the figures, like or functionally equally acting components are denoted by the like reference symbol.

In FIG. 1, a first embodiment of a semifinished product HZ will be described in the following. The semifinished product HZ is shown in FIG. 1 in a perspective side view. The semifinished product comprises a base block GK, which has a channel KA that passes through the base block GK. Consequently a first outlet opening AO1 and a second outlet opening AO2 are formed in the base block GK. In the vicinity of the first outlet opening AO1, a hollow cylindrical anchoring element VA is formed on the inside face IF of the channel KA.

The base block GK is formed from a thermoplastic synthetic material, which encloses the anchoring element VA over its full surface. The anchoring element can be produced, for example, by injection molding into the thermoplastic synthetic material of the base block GK. In order to achieve a high stability between the anchoring element VA and the base block GK, the anchoring element VA can be furnished on its outside, i.e. the side facing the channel KA, with several grooves RI. Furthermore, it is also provided that the anchoring element VA is additionally furnished above the grooves RI with a coating, which is formed from the thermoplastic synthetic material.

In FIG. 2, a second embodiment of the semifinished product HZ according to the invention is shown, again in a perspective side view. In this embodiment the anchoring element VA is additionally furnished with, protruding out of the base block GK, a base element BE, which is formed, for example, as a holding pin introducible into an implant or already as an implant anchorable in a jawbone. For this purpose the base element BE may either have a non-rotationally-symmetric cross section, which is formed, for example, by a corresponding profiling, or be furnished with a helical profile.

In FIG. 3, the semifinished product HZ from FIG. 1 is shown in a further embodiment. In addition to the components already described in FIG. 1, the semifinished product HZ has a holding element HE which, through the channel KA, is joined to the base block GK by means of a screw SC. The holding element HE functions as a clamping aid in a machining device.

The holding element HE is shown once again in FIG. 4, in enlarged representation. The holding element HE may be adhesively bonded onto the semifinished product HZ, wherein an adhesive joint KL is formed between the base block GK and the holding element HE. In the region of the adhesive joint KL, the holding element HE may be furnished with a coating BS. This coating BS consists of the thermoplastic synthetic material of the base block GK, and so a good adhesive joint can be established between the holding element HE and the base block GK. Beyond this, it is also possible to injection-mold the holding element HE already in the base block GK, similarly to the anchoring element VA or to the base element BE.

In the embodiment according to FIG. 3, the holding element HE and the channel KA are disposed to engage axially one inside the other. Accordingly, the holding element HE and the channel KA are aligned with one another, i.e. disposed in the same orientation. In many application situations, however, it is advantageous when the holding element HE does not coincide with the axis of the channel KA. Then it may be provided in particular that the longitudinal axes of the holding element HE and of the channel KA have a right angle relative to one another. An embodiment of the semifinished product HZ according to the invention, in which the channel KA and a longitudinal axis of the holding element HE enclose a right angle, is shown in FIG. 5. In this case the holding element HE is again adhesively bonded to the base block GK, in which case it is likewise possible to injection-mold the holding element HE already into the base block GK. The configuration of the channel KA shown in FIG. 3 is usually referred to as the A-axis, whereas the embodiment shown in FIG. 5 is referred to as the Y-axis. In the embodiment according to FIG. 5, the anchoring element VA is disposed in the interior of the channel KA—which again has two outlet openings AO1 and AO2—in the vicinity of the first outlet opening AO1.

In FIG. 6, a further embodiment of the semifinished product according to the invention is shown, wherein this embodiment in turn corresponds to the rotated channel axis KA according to FIG. 5, in which case the fastening element BE is now also additionally present, as was already described in connection with FIG. 2.

The anchoring element as shown in FIGS. 1 to 6 is usually made of titanium or of a titanium alloy. In general, the use of other non-noble metals is also possible. Likewise it is possible to produce the anchoring element VA from a ceramic, for example aluminum oxide or zirconium dioxide. A further option could consist in applying, on the inside face IF of the channel KA, a fiber-reinforced material suitable for dental purposes, which then forms the anchoring element VA.

The base element BE is usually likewise made of titanium or of a titanium alloy, in which case the use of other non-noble metals or of the above-mentioned ceramics is also possible here. The base element BE and the anchoring element VA may also be formed in one piece.

In FIG. 7, a further embodiment of the semifinished product HZ is shown in which the anchoring element VA and the base element BE are already positioned as separate components. In FIG. 7, the semifinished product HZ is shown in a top view, wherein the semifinished product HZ is illustrated in cutaway view in the region of the first outlet opening AO1 in the plane of the drawing. It will be recognized that the anchoring element VA is provided on its outside with grooves RI, which form a joint between the anchoring element VA and the channel KA.

The base element BE, which is illustrated individually once again in FIG. 8, has on the side facing the anchoring element a surface structure OS, which is formed, for example, as a cylindrical recess. The anchoring element VA has a similar corresponding surface structure OS, so that the base element BE and the anchoring element VA can fit one into the other. In this embodiment the base element BE can be adhesively bonded into the anchoring element VA in simple manner. Substantially, the holding pin HS protrudes out of the base block GK, so that an abutment, for example, is formed after machining of the base block GK.

The formation of an abutment AB is explained once again by way of example in FIGS. 9 and 10. In this connection, FIG. 9 is a representation of the semifinished product HZ with a base block GK, which is illustrated in cutaway view in the region of the anchoring element VA. By removal of material from the base block GK, the abutment AB, for example, can be formed, as is indicated in FIG. 10.

Up to now the joint between the base element BE and the anchoring element VA has been established adhesively. It is also entirely possible, however, to provide the joint between the base element BE and the anchoring element VA mechanically, i.e. with retentive elements. This retention mechanism may be used in addition to or instead of the adhesive joint.

An example of a base element BE that is provided with the retentive elements is shown in FIGS. 11 (A) to (C). In FIG. 11 (A), the base element BE is shown in a sectional view. The base element BE is provided on the side subsequently facing the anchoring element VA with the surface structure OS. An interlock VR, which may be used as a retention mechanism, is disposed on side faces in a direction that is defined perpendicular to the channel axis.

In FIG. 11 (B), the base element BE is illustrated in the direction of the channel axis, wherein the interlocks VR are able to engage in corresponding openings OE of the anchoring element VA, so that a mechanical fastening of the base element BE in the anchoring element VA is created by turning.

In FIG. 11 (C), the positioning of the base element BE that corresponds to an opened condition of the interlock between base element BE and anchoring element VA is shown. In this case the interlocks VR correspond with the openings OE, so that the base element BE can be incorporated into the anchoring element VA.

The interlocking mechanism described in connection with FIGS. 11 (A) to (C) ensures an additional mechanical loadability when the semifinished product is exposed to high forces in a dental prosthetic arrangement. This locking mechanism corresponds substantially to a quarter-turn lock.

The thermoplastic synthetic material as PEEK or PEKK, respectively, or PAEK, may be chosen as the thermoplastic synthetic material both for the formation of the base block GK and for the above-described coatings of the anchoring element VA as well as of the holding element HE. From this synthetic material, it is possible, by milling or grinding of the base block GK in an appropriate machining device, to produce abutments, implants or even crowns of almost any desired shape. The said synthetic materials are biocompatible and exhibit a very high stability. The synthetic material may be applied onto the anchoring element VA by pressing, for example, wherein preferably heating in a temperature range between 380° C. and 400° C. is carried out. This temperature has proved to be particularly effective, and it lies above the melting point of PEEK but below that temperature range in which a degradation of the materials used would begin. In the hot-pressing step, a gap-free enclosure of the anchoring element VA is achieved, wherein the grooves RI function as retentive regions, which favors a shrink coating after cooling of the synthetic material. Moreover, molecular chains of the PEEK are able to bond with superficially oxidized titanium of the anchoring layer VA. This chemical bonding supports the adhesion of the synthetic material over the anchoring element VA, so that a substantially full-surface covering of the anchoring element VA with the synthetic material is achieved.

In FIG. 12 a further embodiment of a semifinished product HZ according to the invention is shown. This embodiment shows a multi-colored structure of the base block GK. In the exemplary embodiment shown, the thermoplastic material forming the base block GK is tinted in two colors, for example white and pink. The different colors meet at the separating line TR. Accordingly, it is possible to create a two-colored or if necessary even multi-colored semifinished product HZ, so that the visual impression is correspondingly altered, especially for use in a front-teeth region.

In FIG. 13, an abutment AB is shown in which the base block GK exists no longer as a block but has already been made as a dental prosthetic arrangement. As an example, an upper region AB1 functions as the seating for a crown. The upper region AB1 has a white color, so that a visually appropriate product is obtained after adhesive bonding of the crown. In a lower region AB2, the abutment has, for example, a gum-colored tint. Beyond this, the abutment is furnished with the anchoring element VA, which is covered in the upper region AB1 and in the lower region AB2 by the thermoplastic synthetic material of the base block GK. The anchoring element VA may have, in a manner common in the art, a screw channel for an occlusal screwed joint with an end facing the upper region AB1 and a seating in an implant at an end facing the lower region AB2. The abutment AB may either be made from the base block of a semifinished product HZ as described hereinabove in FIG. 12 or else may even be injection-molded or pressed onto the anchoring element VA. Such an abutment AB is produced individually or made in advance.

The features in the foregoing and those specified in the claims as well as those inferable from the figures are advantageously realizable both individually and in various combinations. The invention is not limited to the described exemplary embodiments but is modifiable in many ways within the scope of expertise of those skilled in the art.

The invention claimed is:

1. Semifinished product for the fabrication of dental prosthetic arrangements, especially of one-colored or multi-colored abutments, comprising a one-colored or multi-colored base block (GK), which has, passing through the base block (GK), a channel (KA), on the inside face (IF) of which a hollow-cylindrical anchoring element (VA) is formed, wherein the base block (GK) covers the anchoring element (VA) with a thermoplastic synthetic material in one-colored or multi-colored form at least partly over the full surface via a hot processing step, wherein the anchoring element (VA) is furnished with a base element (BE) protruding out of the base block (GK), and wherein the base block (GK) is joined to a holding element (HE), which is used as a holder in a machining device, wherein the base element is provided with at least one interlock (VR) and the anchoring element (VA) is provided with at least one opening (OE) corresponding to the interlock (VR), so that the anchoring element (VA) is connected to the base element (BE) by inserting the base element into the anchoring element and turning the base element (BE) until the interlock (VR) seats within the opening (OE).

2. Semifinished product according to claim 1, in which the anchoring element (VA) is furnished with a coating, wherein the coating is applied on a side facing away from the inside surface (IF).

3. Semifinished product according to claim 1, in which the anchoring element (VA) has a roughened surface on a side facing the inside surface (IF).

4. Semifinished product according to claim 1, in which the anchoring element (VA) is made of a non-noble metal, of a ceramic, or of a fiber-reinforced material suitable for dental purposes.

5. Semifinished product according to claim 1, in which the base element (BE) is provided with a holding pin, introducible into an implant, which has a non-rotationally-symmetric cross section, or comprises an implant anchorable in a jawbone or another bone topography.

6. Semifinished product according to claim 1, in which the base element (BE) is made of a non-noble metal-of a ceramic, or of a material suitable for dental purposes.

7. Semifinished product according to claim 1, in which the holding element (HE) and the channel (KA) are disposed to engage axially one inside the other, so that the holding element (HE) and the channel (KA) are aligned with one another.

8. Semifinished product according to claim 7, in which the holding element (HE) and the channel (KA) have a different direction along their longitudinal axes.

9. Semifinished product according to claim 1, in which the holding element (HE) is injection-molded into the base block (GK) or is formed in one piece together with the one-colored or multi-colored base block (GK).

10. Semifinished product according to claim 1, in which the holding element (HE) is adhesively bonded with the base block (GK), so that an adhesive joint (KL) is obtained between the base block (GK) and the holding element (HE).

11. Semifinished product according to claim 10, in which the holding element (HE) is furnished at least on the side facing the adhesive joint (KL) with a coating.

12. Semifinished product according to claim 1, in which the thermoplastic synthetic material is PEEK, PEKK or PAEK.

* * * * *